United States Patent
Wintergerste et al.

(10) Patent No.: US 8,651,731 B2
(45) Date of Patent: Feb. 18, 2014

(54) DYNAMIC MIXER

(75) Inventors: Torsten Wintergerste, Greifensee (CH); Hubert Holdener, Kriens (CH); Percy Leue, Singen (DE)

(73) Assignee: Sulzer Mixpac AG, Haag (CH)

( * ) Notice: Subject to any disclaimer, the term of this patent is extended or adjusted under 35 U.S.C. 154(b) by 795 days.

(21) Appl. No.: 12/676,466

(22) PCT Filed: Jun. 6, 2008

(86) PCT No.: PCT/EP2008/057049
§ 371 (c)(1),
(2), (4) Date: Mar. 4, 2010

(87) PCT Pub. No.: WO2009/033832
PCT Pub. Date: Mar. 19, 2009

(65) Prior Publication Data
US 2010/0208544 A1    Aug. 19, 2010

(30) Foreign Application Priority Data

Sep. 10, 2007    (CH) ..................................... 1412/07

(51) Int. Cl.
*B01F 7/20* (2006.01)
(52) U.S. Cl.
USPC .................... 366/181.4; 366/302; 366/329.1; 366/329.2
(58) Field of Classification Search
USPC .............. 366/181.4, 302, 207, 329.1, 329.23; 222/145.6
See application file for complete search history.

(56) References Cited

U.S. PATENT DOCUMENTS

| 5,249,862 A * | 10/1993 | Herold et al. ................. 366/312 |
| 6,540,395 B2 * | 4/2003 | Muhlbauer et al. ........... 366/307 |
| 6,932,243 B2 * | 8/2005 | Keller ........................ 222/145.6 |

FOREIGN PATENT DOCUMENTS

| DE | 20 00 981 A1 | 11/1970 |
| DE | 100 19 893 A1 | 10/2001 |
| DE | 101 64 385 C1 | 3/2003 |
| DE | 10 2004 008 748 A1 | 9/2004 |
| EP | 1 099 470 A1 | 5/2001 |
| JP | 6-226178 A | 8/1994 |
| WO | WO 98/43727 A1 | 10/1998 |

* cited by examiner

*Primary Examiner* — David Sorkin
(74) *Attorney, Agent, or Firm* — Kilpatrick Townsend & Stockton LLP

(57) ABSTRACT

The invention relates to a dynamic mixer for viscose components in particular for the mixing of dental compositions, with a rotor (30) and a housing (2), which has front inlet openings (12, 13) for the components and at least one rear outlet opening (20) and the inner space of which includes a pre-chamber (17) and a main chamber (22), with the pre-chamber (17) opening into the main chamber (22) in a distal, tapering transition section (16). For the precise regulation of the concentration of the components to be mixed of the supplied components even with temporary concentration fluctuations of the same and in order to achieve a high degree of homogenization, it is proposed that the dynamic mixer (1) has at least one individual channel (23a-d) as a passage from the pre-chamber (17) into the main chamber (22), with the width of the individual channel (23a-d) extending over a part of the periphery of the transition section (16).

18 Claims, 4 Drawing Sheets

DYNAMIC MIXER

CROSS-REFERENCE TO RELATED APPLICATIONS

Figure 1:
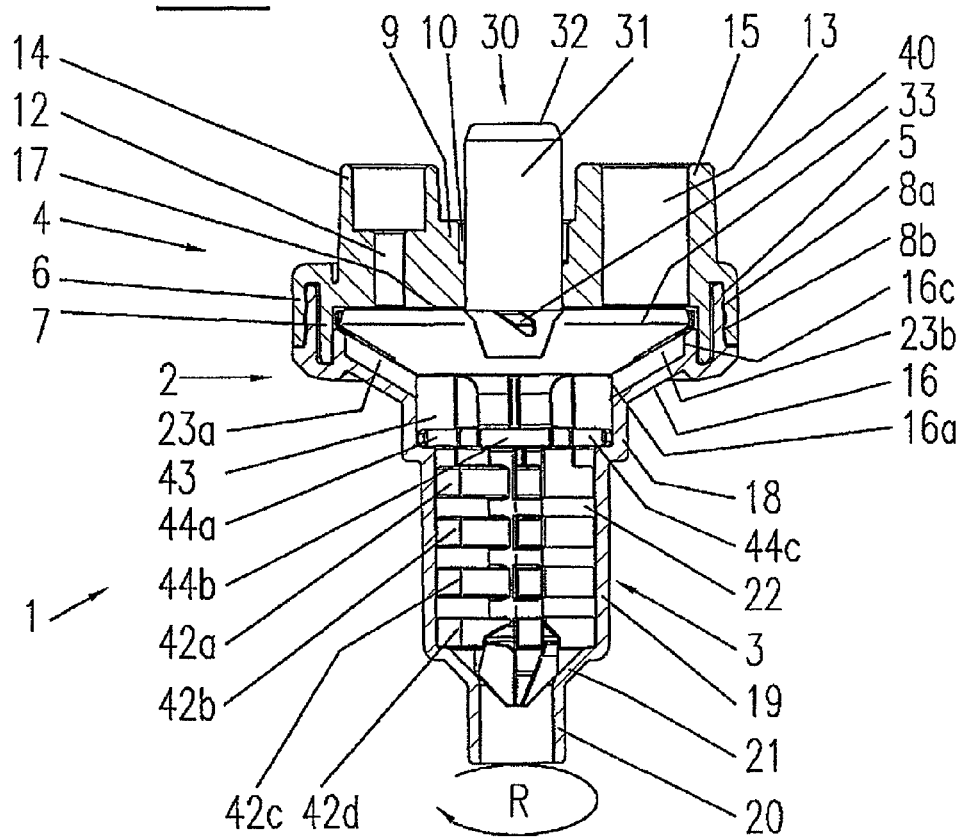

This application is a National Stage of International Application No. PCT/EP2008/057049 filed Jun. 6, 2008, and which claims the benefit of Swiss Patent Application No. 01412/07, filed Sep. 10, 2007, the disclosure of which are incorporated herein by reference.

The invention relates to a dynamic mixer in accordance with preamble of patent claim 1.

A dynamic mixer for the mixing of components with different portions by volume is known from WO 2007/041878 of the same applicant, in particular for the manufacture of molding compositions for dental impressions. A pre-chamber is arranged in the inner space of the mixer housing, within which the mixing rotor has a distribution body for the distribution of the components about its axis of rotation in order to thereby achieve a correct mixing ratio between the components and to avoid air inclusions. Thereafter, the pre-mixed components pass through at least one passage opening into a main chamber for their complete mixing.

The purpose of the subdivision into two separate mixing chambers is that a global homogenization of the component mixture should already be achieved in the pre-chamber, whereas a local homogenization should subsequently take place in the main chamber. This is because, when mixing of two or more components, one requires both a uniform pointwise distribution of the components over the entire flow cross-section on a global plane as well as the smallest possible local deviation from the average concentration on a local plane. In this respect the distribution body admittedly offers an enlargement of the distribution surface for the components, the extent of which is important for the pre-mixing of the components on a global plane; however, the surface enlargement along the rotor axis is restricted as a result of the geometrical constraints along the rotor axis.

In addition to this comes, as an important factor, the longest possible dwell time of the components within the pre-chamber at the start of the mixing process because an initial concentration fluctuation of the components that are supplied is to be expected, in particular for the component with the smaller proportion by volume. Through a suitable dwell time within the pre-chamber, initial concentration deviations of the supplied components can be balanced out and thus a waste with respect to the mixed material initially emerging from the mixer can be avoided. In this respect, in the previously known mixer, the dwell time within the pre-chamber can only be influenced by a selected dimensioning of the passage opening.

DE 100 15 133 C1 discloses a further dynamic mixer having a first mixing rotor of dome shape disposed in the front chamber section, which has cutouts functioning as passages and which extends in its outer radial section along an internal wall of the housing which extends in funnel-like manner. A second mixing rotor is disposed axially behind it with passages arranged in such a way that the passages of the one mixing rotor are covered over by the respective non-free part of the other mixing rotor. In this way a situation is achieved in which material not engaged by the first mixing rotor is engaged with a higher probability by the second mixing rotor.

With a rotor arrangement of this kind a high degree of homogenization of the mixture can be achieved depending on the number of the mixing rotors. However, little account is taken of an initial deviation in concentration of the supplied components. Because the dwell time of the components that are supplied at each of the mixing rotors can only be positively influenced by a dimensioning of the respective cutouts, which is as small as possible, because the areal extent of the one mixing rotor must correspond to the size of the cutouts of the other respective mixing rotor or exceed it. This enables only a comparatively short dwell time at the respective mixing rotor so that temporary concentration fluctuations can hardly be compensated for. Moreover, a considerable deterioration of the initial mixing ratio must be expected, above all by the material component which is only engaged by one of the two mixing rotors.

Starting from this, the invention is based on the object of further developing a dynamic mixer of the initially named kind in such a way that a precise regulation of the concentration of the components supplied is ensured, even with temporary concentration fluctuations of the same, with a simultaneously high degree of homogenization on a global plane and on a local plane, while avoiding the above named disadvantages, with the constructional length of the dynamic mixer also being minimized by increased efficiency by at least one mixing stage.

The named object is satisfied by a dynamic mixer in accordance with patent claim 1. Through the peripheral arrangement of individual passages, the volume flow between the pre-chamber and the main chamber takes place in a controlled manner in accordance with the invention only in these local regions. This results in an extended dwell time of the components in the pre-chamber so that temporary concentration fluctuations of the supplied components can be compensated.

In a preferred embodiment in accordance with patent claim 6 at least one large area mixing rotor with passage openings is arranged for the pre-mixing of the components on a global plane in front of the individual passages. In this way the volume flow between the pre-chamber and the main chamber is only possible in accordance with the invention during a temporary areal overlap between the rotating passage openings and the individual channels.

Further preferred embodiments of the invention are respectively defined by the remaining dependent patent claims.

In the following, the invention will be explained with reference to a preferred embodiment in more detail with reference to the drawings by which further properties and advantages of the invention result. The figures, the description and the claims contain numerous features in combination which the person skilled in the art will also consider individually and combine into meaningful further combinations.

Figure 2:
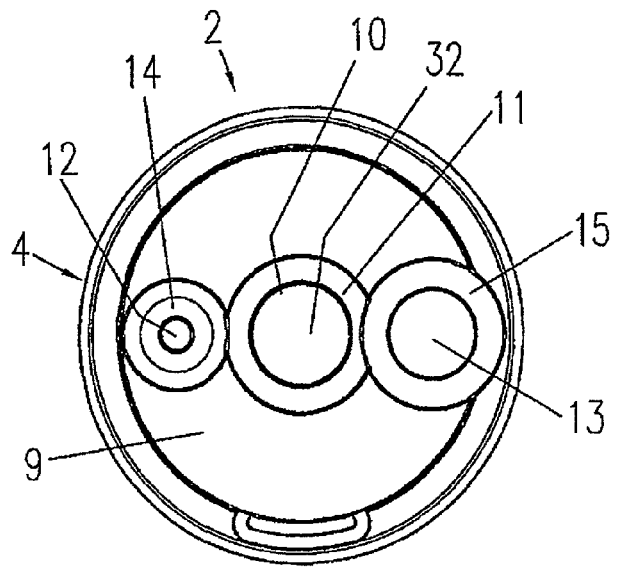
Figure 3:
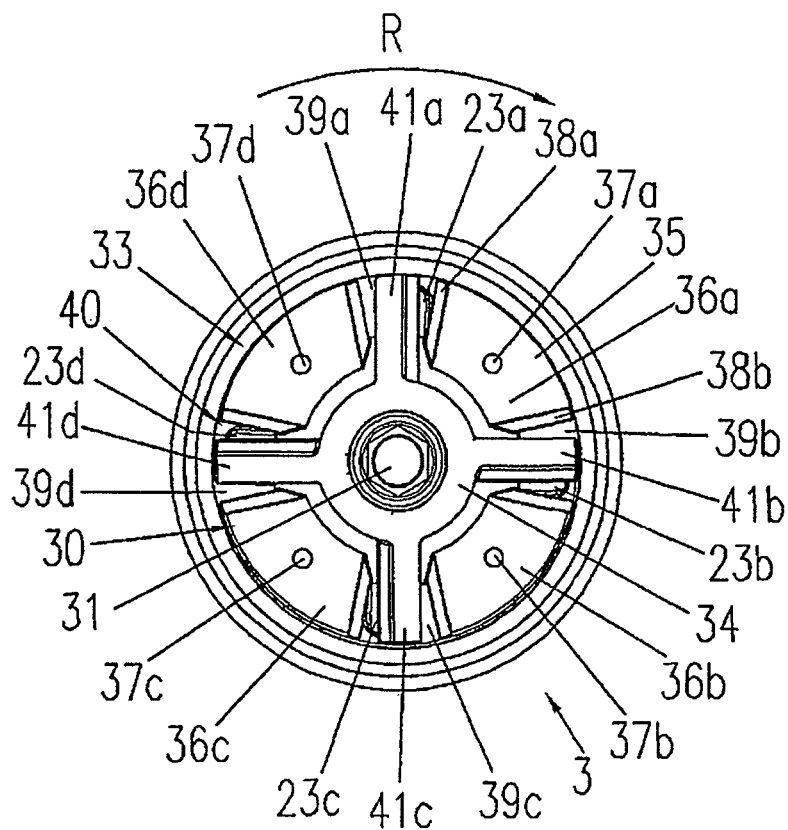
Figure 4:
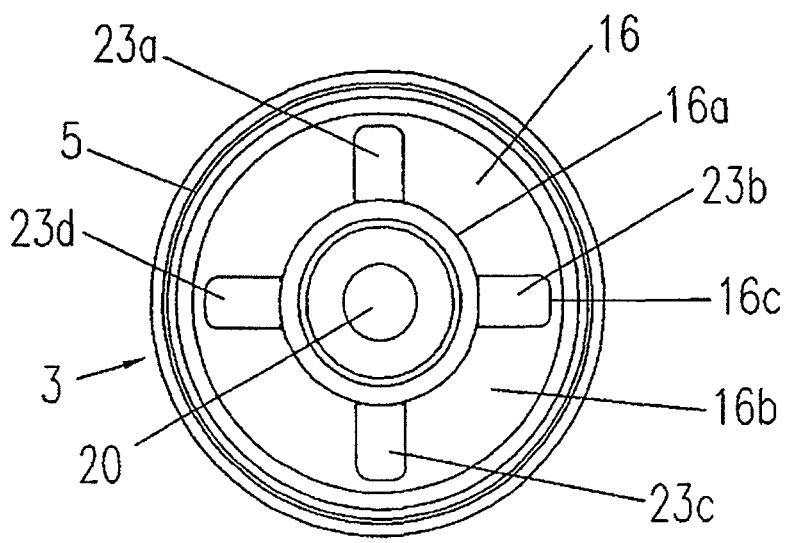
Figure 5:
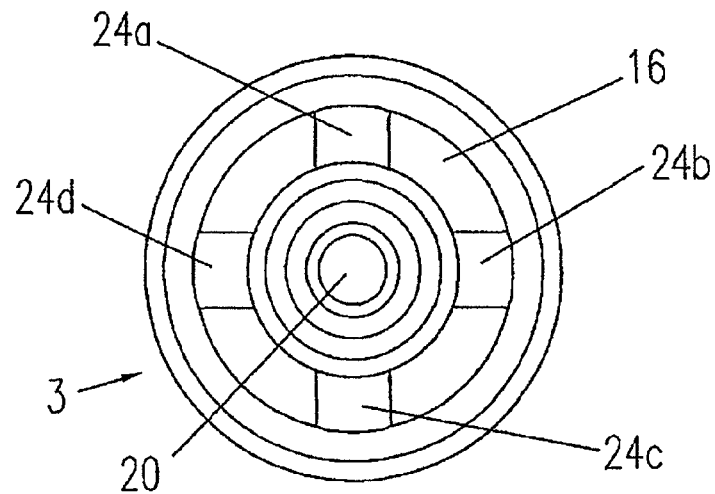
Figure 6:
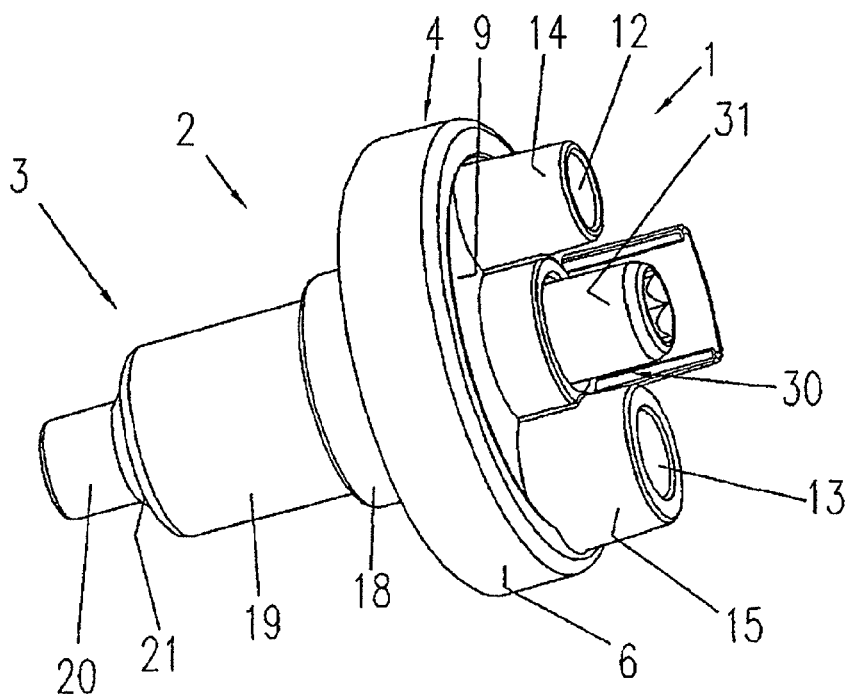
Figure 7:
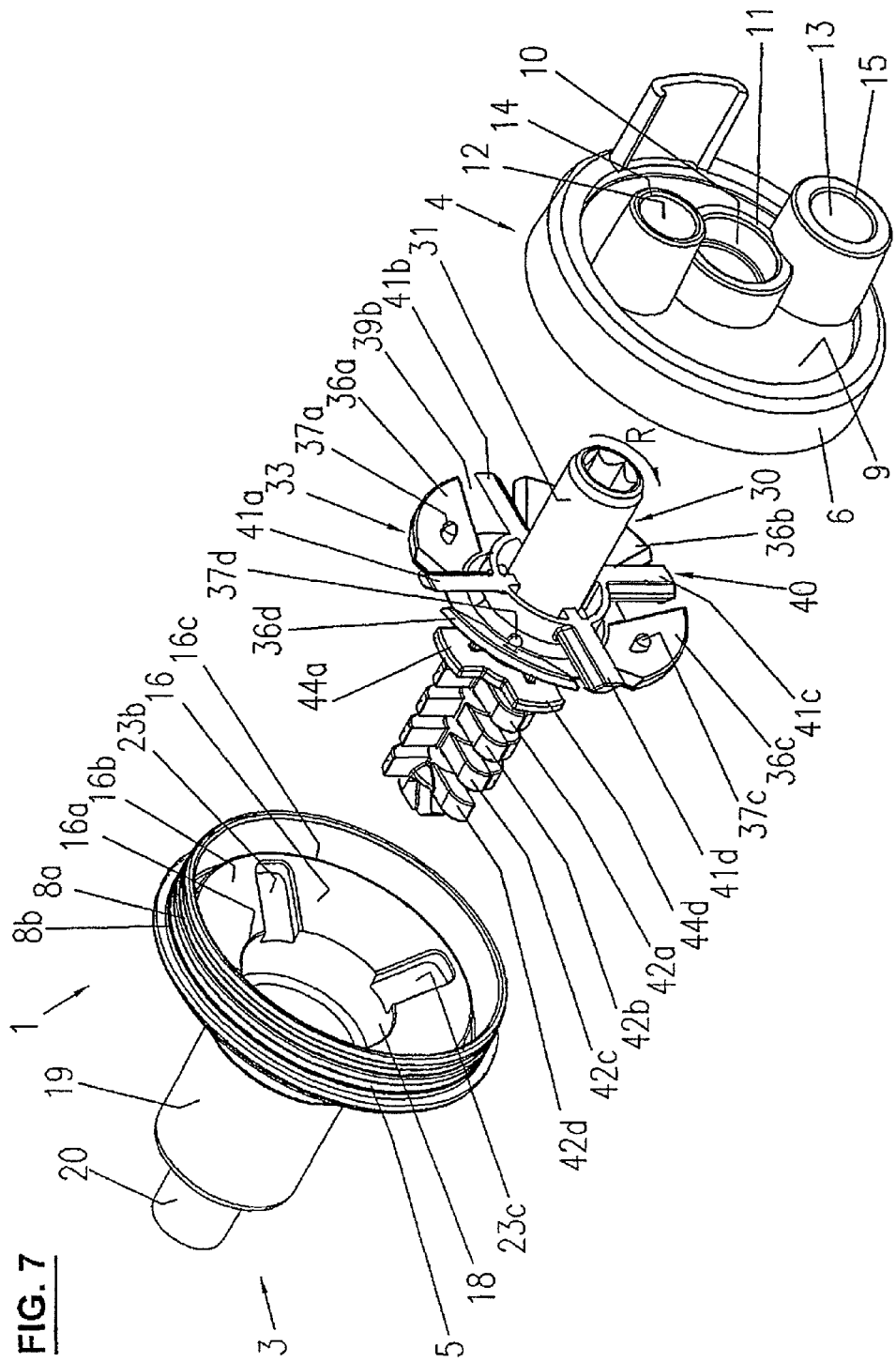

There are shown:

FIG. 1 a side view of a dynamic mixer in accordance with the invention, with the housing being shown in an axial section, FIG. 2 a front view of the dynamic mixer shown in FIG. 1, FIG. 3 the front view shown in FIG. 2 of the dynamic mixer with the cover of the housing having been removed, FIG. 4 the front view shown in FIG. 3 of the dynamic mixer with the rotor having been removed from the housing, FIG. 5 a rear view of the dynamic mixer shown in FIGS. 1 and 4, FIG. 6 a perspective view of the dynamic mixer shown in FIGS. 1 to 5 and FIG. 7 an exploded illustration of the dynamic mixer shown in FIGS. 1 to 6.

A dynamic mixer 1 shown in FIGS. 1 to 7 includes a housing 2 having a housing body 3 which is sealingly closeable at the front side by a cover 4. For this purpose, the cover 4 has a cylindrical outer wall 6 and a cylindrical inner wall 7 with mutual radial spacing into which a cylindrical sealing lip 5 engages which is present in the housing body 3 at the front side. Ring-like cutouts 8a, 8b are provided along the outer periphery of the sealing lip 5 into which corresponding projections formed along the inner side of the outer wall 6 of the lid 4 latch in shape-locked manner.

A circular disc-like front wall 9 of the cover 4 has a concentric rotor opening 10 which is surrounded at the outer side by a cylindrical mount or nose 11 with a fractionally larger internal diameter. Respective inlet openings 12, 13 for the components to be mixed are present in the front wall 9 of the cover 4 at two opposite sides adjacent the rotor opening 10. The inlet openings 12, 13 are of different sizes, with the inlet opening 12 having the smaller diameter being provided for the supply of a component with a smaller proportion by volume during the mixing of the components. The inlet openings 12, 13 are respectively bounded at the outer side of the cover by a cylindrical mount 14, 15 for cartridges with the respective components. The internal diameter of the mount 14 has a larger internal diameter than the smaller inlet opening 12, whereas the larger inlet opening 13 and the internal diameter of its mount 15 are of the same size.

A conically tapering transition section 16 adjoins the axially extending sealing lip 5 in the housing body 3. The inner space bounded by the inner walls of the cover 4 and of the transition section 16 forms a pre-chamber 17 within which a premixing of the components takes place with respect to a global homogenization of the mixture.

At its rear end the transition section 16 opens into an axially extending short cylinder section 18 of the housing body 3. Behind the short cylinder section 18 there is a long cylinder section 19 with a smaller internal diameter adjoining the short cylinder section 18 after an abrupt step-like taper. A cylindrical outlet opening 20 is arranged at the rear end of the long cylinder section 19 after a further conical taper 21. The inner space of the housing body 3, which is bounded by the inner side edge 16a of the transition section 16 and also by the inner walls of the short and long cylinder sections 18 and 19, corresponds to a main chamber 22 for the through-mixing of the components on a local plane.

Four individual cutouts 23a-d are formed peripherally along the inner wall 16b of the transition section 16. The recesses 23a-d extend from the point of view of their length radially and obliquely rearwardly essentially over the entire transition section 16 and border at their front closed end at an outer side edge 16c of the transition section and are open at their rear end in the region of the inner side edge 16a so that they open from the pre-chamber 17 into the main chamber 22. The width of the recesses 23a-d extends only in each case over a part of the periphery of the transition section 16. In this connection, adjacent recesses 23a-d have respectively the same spacing in the peripheral direction of the transition section 16. Individual channels 23a-d for the premixed components are provided by the recesses and enable a passage from the pre-chamber 17 into the main chamber 22. As can be seen from FIG. 5, corresponding local projections 24a-d are present at the outer side of the housing wall corresponding to the inner side recesses 23a-d.

The described housing 2 has a length of ca. 6 cm and a width at its front side of ca. 4 cm and consists of injection-molded plastic.

A rotor 30 is arranged in the housing 2. The rotor 30 has a rotor axle 31 which projects through the rotor opening 10 and the cylindrical mount 11 in the front wall 9 of the cover 4 and can be coupled in this way at its front free end 32 to a mixer drive shaft.

A rear mixing rotor 33 with vanes is arranged on the rotor axle 31 in the rear region of the pre-chamber 17. The inner rotor section 34 of the rear mixing rotor 33 has the shape of a radially extending flat circular disc which is disposed concentrically around the rotor axle 31. An outer rotor section 35 with vanes adjoins the outer periphery of the inner rotor section 34 and includes four vanes or blades 36a-d which respectively have the shape of a bent circular ring segment. The vanes or blades 36a-d are uniformly spaced and are obliquely inclined to the front from a radial point of view starting from the inner rotor section 34 so that the outer section 35 has a radially inwardly directed depression at its inlet side. Through the plate shape which is achieved in this way the rear mixing rotor 33 serves as a temporary receiving basin during the concentration regulating and premixing process for the components.

Respective eddy inducing elements 37a-d in the form of an axial spigot-like projection is disposed in the central region of each of the vanes 36a-d. The two side edges 38a, b at each of the rotor vanes 36a-d are chamfered off towards the rear. Four passage openings 39a-d for the components are provided by the same sized spacing of respectively adjacent rotor vanes 36a-d in the peripheral direction of the rear mixing rotor.

The outer contour of the so formed rear mixing rotor 33 is matched to the inner wall 16b of the transition section 16, with the inclination and length of the vanes 36a-d corresponding substantially to that of the inner wall 16b of the transition section 16 and the short cylinder section 18 arranged behind it corresponding in its radial cross-section essentially to the inner rotor section 34. In this way a sealing off of the pre-chamber 17 from the main chamber 22 is achieved so that a passage of the components only takes place through the passage openings 39a-d and the individual passages 23a-d arranged therebehind. In this connection the width of the passage openings 39a-d and the width of the individual channels 23a-d lies in approximately the same order of magnitude, with the passage openings 39a-d preferably being fractionally larger. A minimum axial spacing between the inner wall 16b of the transition section 16 and the rear mixing rotor 33 avoids strong rubbing of these elements during the rotation of the axle 31 and material scrapings along the inner wall caused by a wall motion of the mixing rotor.

Within the pre-chamber 17 the rotor 30 includes a front mixing rotor 40 disposed in front of the rear mixing rotor 33 in the axial direction. The front mixing rotor 40 has four substantially bar-like mixing vanes 41a-d. The mixing vanes 41a-d extend radially from the rotor axle 31 with a length which, when viewed radially, extends up to the outer periphery of the rear mixing rotor 33 arranged behind it. In this they terminate from the inside at the inner wall 7 of the cover 4 without scraping along the wall. In this respect the mixing vanes 40a-d are respectively arranged in front of the passage openings 39a-d so that their axial projection surface respectively projects into one of the passage openings 39a-d. The width of the mixing vanes 40a-d is smaller than the width of the passage openings 39a-d so that the passage openings 39a-d are not covered over, as is in particular evident in the front view in FIG. 3. The axial cross-sectional area of the mixing vanes 40a-d has a trapezoidal form, with axially extending sides of a respective vane 41a-d being made with an inclined surface in such a way that they have a gradient in the direction of rotation A of the mixing vane. In this connection the rear side has a lesser gradient and is made with a larger area.

Within the main chamber 22 the rotor 30 has five further vaned mixing rotors 42a-d, 43. The mixing rotor 33 is arranged at the end of the short cylinder section 18 and borders at the side and at the rear at the step-like taper between the short cylinder section 18 and the long cylinder section 19 without scraping along wall. In this connection the mixing rotor 43 consists of four vanes 44a-d which are of substantially square shape in an axial view which are each preferably peripherally arranged in a region in which the rear mixing rotor 33 in the pre-chamber 17 has the passage openings 39a-d. The vanes 44a-d project, however, in the radial direction not beyond the outer periphery of the inner rotor section 34 of the rear mixing rotor 33. The vanes 44a-d are connected to one another in their starting section through a peripheral ring-like projection around the rotor axle 31.

In the direction of axial extent of the subsequent long cylinder section 19, four further mixing rotors 42a-d are provided each having four vanes. All vanes of the mixing rotors 42a-d are of identical shape and have in the radial direction a substantially jagged shape which is rounded off at the front side in the direction of rotation R. In the axial direction they are made longer than the vanes 44a-d. The vanes of the mixing rotors 42a-d border on the inner wall of the long cylinder section 19 without scraping along this wall. In this connection they are arranged peripherally aligned with respect to the vanes of subsequent mixing rotors 42a-d, with the arrangement respectively extending behind one of the vanes 44a-d of the mixing rotor 43. Four axially extending elongate projections of the rotor axle 31 extend from the rear side of the rear mixing rotor 33 through the respective vanes 44a-d up to the respective vanes of the front most of the mixing rotors 42a-d.

During the mixing process, the component with the smaller proportion by volume is pressed through the small inlet opening 12 and the component with the higher proportion by volume through the larger inlet opening 13 into the pre-chamber 17. During the passage of the front mixing rotor 40, a first eddying is in particular brought about of the component with the smaller proportion by volume, whereupon the components meet the plate-like surface of the rear mixing rotor 33.

Through the limited width of the individual passages 23a-d, which are moreover only temporarily opened—namely during an axial overlap with the passage openings 39a-d of the rotating rear mixing rotor 33—the discharge of the components from the pre-chamber 17 to the main chamber 22 is delayed. By a suitable choice of the number and dimensioning of individual channels 23a-d and also of the passage openings 39a-d, the dwell time of the components on the plate-like surface of the rear mixing rotor 33 can be set almost arbitrarily in a wide range. In this way a situation can, for example, be achieved in which the pre-chamber has first to be almost completely filled with the supplied components at the start of the mixing process before the components enter into the main chamber.

Thanks to the large area design of the rear mixing rotor 33 the concentration of the respective components of the mixture is regulated with a high accuracy in this period of time and at the same time a pre-mixing is carried out in order to achieve in this way a global homogenization of the mixture. The latter is in particular improved by the elements 37a-d on the vane blades 36a-d which cause an eddying of the components or of the pre-mixture during the movement along the surface of the rear mixing rotor 33.

At the same time, the shearing action of the front mixing rotor 40 with the chamfered axial side edges of its mixing vanes 41a-d contribute to the pre-mixing process. Since its axial projection surface projects in each case into a passage opening 39a-d of the rear mixing rotor 33, a situation is prevented in which the supplied components can enter directly into the passage openings 39a-d without meeting the outer or inner rotor section 35 and 34 respectively. The larger area rear side edge of the mixing vanes 41a-d moreover serves for a deviation of the pre-mixed composition in the direction of the passage openings 39a-d and for a supply to the individual channels 23a-d.

In this way a high global degree of homogenization of the mixture is already achieved in the pre-chamber 17. In this way the number of the mixing rotors 42a-d, 43 in the main chamber 22 can be kept small, while nevertheless obtaining an excellent global degree of homogenization of the mixture on emerging through the outlet opening 20. This leads to a cost-saving and space-saving design of the mixer 1, in particular with respect to the total axial length of the same.

Numerous modifications are accessible to the person skilled in the art from the description of the preferred embodiment without departing from the scope of protection of the invention which is defined by the claims.

Thus, the number of individual channels 23a-d need not necessarily correspond to the number of passage openings 39a-d in order to obtain the desired dwell time of the mixture in the pre-chamber 17. Furthermore, the transition section 16 does not have to be realized as an integral component of the housing 2. For example, it can also be a distally tapering element in the inner space of the housing 2.

Furthermore, it is conceivable that the individual channels 23a-d and/or the passage openings 39a-d vary in their width, in particular having an increasing or reducing width along the transition section 16 in order in this way to regulate the desired volume flow from the pre-chamber 17 into the main chamber 22. Their depth can likewise vary.

Furthermore, the individual channels 23a-d can also have a peripherally oblique position along the transition section 16 in addition to their extent directed radially towards the centre and obliquely towards the rear so that the volume flow of the components from the pre-chamber 17 into the main chamber 22 also has a peripheral direction component in addition to a central direction component.

Moreover, more than only one further component with a smaller proportion by volume can be mixed with the component with the higher proportion by volume. In this case, a further inlet is required in the front wall 9 of the cover 4. Furthermore, the design of the dynamic mixer 1 also has advantages if the components have the same mixing ratio, in which case inlet openings 12, 13 of the same size are to be provided.

The constructional length of the mixer housing 2 can vary depending on the nature and number of components to be mixed and the number of the mixing stages which is to be provided. For example, with a mixer for the manufacture of molding compositions for dental impressions, a total length between 3 cm and 10 cm is conceivable.

| Reference Numeral List | |
|---|---|
| 1 | dynamic mixer |
| 2 | housing |
| 3 | housing body |
| 4 | cover |
| 5 | sealing lip |
| 6 | outer wall of cover |
| 7 | inner wall of cover |
| 8a, b | cutouts |
| 9 | front wall of cover |
| 10 | rotor opening |
| 11 | cylindrical mount |
| 12 | small inlet opening |
| 13 | large inlet opening |
| 14 | mount for the small inlet opening |
| 15 | mount for the large inlet opening |

-continued

| Reference Numeral List | |
|---|---|
| 16 | transition section |
| 16a | inner side edge of the transition section |
| 16b | inner wall of the transition section |
| 16c | outer side edge of the transition section |
| 17 | pre-chamber |
| 18 | short cylinder section |
| 19 | long cylinder section |
| 20 | outlet opening |
| 21 | outlet side taper |
| 22 | main chamber |
| 23a-d | individual channels |
| 24a-d | projections |
| 30 | rotor |
| 31 | rotor axle |
| 32 | front free end of the rotor |
| 33 | rear mixing rotor |
| 34 | inner rotor section |
| 35 | outer rotor section |
| 36a-d | vanes |
| 37a-d | eddy inducing elements |
| 38a, b | side edge of the vanes |
| 39a-d | passage openings |
| 40 | front mixing rotor |
| 41a-d | vanes |
| 42a-d | mixing rotor |
| 43 | mixing rotor |
| 44a-d | vanes |
| R | direction of rotation of the rotor |

The invention claimed is:

1. A dynamic mixer for low viscosity to high viscosity components, having
   a rotor; and,
   a housing, which has front inlet openings for the components and at least one rear outlet opening and the inner space of which includes a pre-chamber and a main chamber,
   with the pre-chamber opening into the main chamber in a distal, tapering transition section, the tapering transition section comprising a conical surface extending between the pre-chamber and the main chamber, the conical surface being disrupted by at least one channel as a passage from the pre-chamber into the main chamber,
   wherein the at least one channel comprises a surface opening on the conical surface, the surface opening extending between a closed end and an open end, the open end opening into the main chamber with the width of the at least one channel extending over a part of the periphery of the transition section,
   wherein the length of the at least one channel extends axially over essentially the entire transition section and
   wherein a portion of the rotor has at least one opening configured to align and coordinate with the at least one channel such that a volume flow of the components to the main chamber from the pre-chamber through the transition section occurs only from the opening in the rotor into the surface opening on the conical surface and out through the open end of the at least one channel.

2. A dynamic mixer in accordance with claim 1, comprising at least two channels.

3. A dynamic mixer in accordance with claim 2, wherein adjacent channels each have the same spacing in the peripheral direction of the transition section.

4. A dynamic mixer in accordance with claim 1, wherein the rotor has a rear mixing rotor with an outer rotor section within the pre-chamber, the outer rotor section being arranged axially in front of the transition section, with the at least one passage opening being formed in the outer rotor section.

5. A dynamic mixer in accordance with claim 4, wherein the outer rotor section has a radially inwardly directed depression at the inlet side.

6. A dynamic mixer in accordance with claim 4, wherein the outer rotor section is disposed at the outlet side along the inner wall of the transition section in a minimum axial spacing avoiding friction.

7. A dynamic mixer in accordance with claim 4, further comprising a concentric inner rotor section of the rear mixing rotor, with the inner rotor section having at the inlet side a surface which extends substantially flatly in the radial direction.

8. A dynamic mixer in accordance with claim 4, wherein the number of the at least one passage openings corresponds to the number of the at least one channels.

9. A dynamic mixer in accordance with claim 4, wherein the width of at least one passage opening and/or the peripheral spacing of adjacent passage openings in each case corresponds substantially to those of the at least one channels.

10. A dynamic mixer in accordance with claim 4, wherein the at least one passage opening respectively extends up to the outer margin of the outer rotor section.

11. A dynamic mixer in accordance with claim 4, wherein the length of the at least one passage opening in each case extends substantially radially over the entire outer rotor section.

12. A dynamic mixer in accordance with claim 4, wherein an oblique edge is in each case formed in the outer rotor section along the lateral boundaries of at least one passage opening.

13. A dynamic mixer in accordance with claim 4, wherein axially extending eddy generating elements are arranged at the inlet side surface of the outer rotor section.

14. A dynamic mixer in accordance with claim 4, wherein the rotor inside the pre-chamber has a front mixing rotor with at least one radially extending vane, the axial projection surface of which projects in each case into at least one passage opening of the rear mixing rotor.

15. A dynamic mixer in accordance with claim 14, wherein the number of the vanes of the front mixing rotor corresponds to the number of the at least one passage openings of the rear mixing rotor.

16. A dynamic mixer in accordance with claim 14, wherein the axially extending sides of a respective vane are made with an oblique surface in such a way that they have a gradient in the direction of rotation (R) of the mixing rotor.

17. A dynamic mixer in accordance with claim 1, wherein the rotor is located inside the main chamber and has a plurality of a peripherally aligned mixing rotors with separated vanes.

18. A dynamic mixer in accordance with claim 17, wherein the rotor has a mixing rotor with separated vanes within the main chamber in front of the peripherally aligned mixing rotors and a radial surface of the separated vans of the rotor is larger than a radial surface of the peripherally aligned mixing rotors.

* * * * *